US006736800B2

(12) United States Patent  
Rindlisbacher

(10) Patent No.: US 6,736,800 B2
(45) Date of Patent: May 18, 2004

(54) CANNULA SUPPORT HAVING A NEEDLE COVERING FUNCTION AND PACKAGING STRUCTURE COMPRISING A CANNULA SUPPORT

(75) Inventor: Christoph Rindlisbacher, Boll (CH)

(73) Assignee: Disetronic Services, AG, Burgdorf (CH)

(*) Notice: Subject to any disclaimer, the term of this patent is extended or adjusted under 35 U.S.C. 154(b) by 0 days.

(21) Appl. No.: 10/308,907

(22) Filed: Dec. 3, 2002

(65) Prior Publication Data

US 2003/0109832 A1 Jun. 12, 2003

(30) Foreign Application Priority Data

Dec. 4, 2001 (DE) .......................................... 101 59 353

(51) Int. Cl.[7] ............................ A61M 5/32; B65D 83/10
(52) U.S. Cl. ........................................ 604/192; 206/365
(58) Field of Search .................................. 604/192, 198, 604/263, 110, 164.08, 177, 162; 206/365

(56) References Cited

U.S. PATENT DOCUMENTS

| 4,820,277 A | * | 4/1989 | Norelli ...................... 604/192 |
| 4,875,896 A | * | 10/1989 | Kurtz ........................ 604/187 |
| 4,966,591 A | * | 10/1990 | Yuen ......................... 604/192 |
| 5,486,163 A | * | 1/1996 | Haynes ..................... 604/192 |
| 5,925,032 A | * | 7/1999 | Clements ..................... 606/1 |
| 5,971,966 A | * | 10/1999 | Lav ........................... 604/263 |
| 6,156,012 A | | 12/2000 | Nathan |
| 6,500,155 B2 | * | 12/2002 | Sasso ........................ 604/177 |

FOREIGN PATENT DOCUMENTS

WO      WO 01/30426 A1      5/2001

* cited by examiner

Primary Examiner—Sharon Kennedy
(74) Attorney, Agent, or Firm—Dorsey & Whitney LLP

(57) ABSTRACT

The invention relates to a cannula support having a needle covering function, which may be connected to an injection or infusion device and forms a receptacle for a cannula, including at least two pivoting side portions which project from said receptacle which may be pivoted towards each other, to form a needle cover covering a proximal end of said cannula. The invention also encompasses a packaging structure for storing and transporting the cannula support.

17 Claims, 4 Drawing Sheets

CANNULA SUPPORT HAVING A NEEDLE COVERING FUNCTION AND PACKAGING STRUCTURE COMPRISING A CANNULA SUPPORT

PRIORITY CLAIM

This application claims the priority of German patent application No. 101 59 353.8, filed on Dec. 4, 2001 with the German Patent and Trademark Office, which is hereby incorporated herein by reference.

BACKGROUND

For administering a dose or doses of insulin, hormone or the like, so-called injection pens are known from the prior art. In some such pens a cannula support is removably attached to the pen. After a dose has been administered one or more times, the cannula support is removed from the injection pen and disposed of. In order to prevent unintentional needle pricking injuries, a needle cover is required which reliably covers the proximal, i.e., front, end of the injection needle.

SUMMARY

It is an object of the present invention to provide a cannula support having a needle covering function, which can be operated simply and reliably and which can be manufactured cost-effectively. Another object is to provide a packaging structure for suitably storing such a cannula support.

These and other objects are solved by a cannula support having a needle covering function, and by a packaging structure for such a cannula support.

In one embodiment, the present invention comprises a cannula support for connection to an injection or infusion device comprising a cannula, the cannula support comprising a receptacle for the cannula and at least two pivoting side portions which project from the receptacle and which may be pivoted towards each other, forming a needle cover covering a proximal end of the cannula. In one embodiment, the present invention encompasses a packaging structure for a cannula support comprising a receptacle having two relatively pivoting side portions each having an end including a connecting element, the packaging structure comprising a tapered truncated packaging body having side walls, a seal for sealing the body, and an accommodating element, wherein when the cannula support is in the packaging structure, the pivoting side portions abut the side walls such that the pivoting side portions are pivoted toward each other and the accommodating element prevents the connecting elements from being connected.

In one embodiment, the present invention comprises a cannula support having a needle covering function, which may be connected to an injection or infusion device and forms a receptacle for a cannula, including at least two pivoting side portions which project from said receptacle which may be pivoted towards each other, to form a needle cover covering a proximal end of said cannula. The invention also encompasses a packaging structure for storing and transporting the cannula support.

In one embodiment, a cannula support in accordance with the invention has at least two pivoting side portions which project from a receptacle for a cannula and which may be pivoted towards each other to form a needle cover, in order to cover a proximal end of a cannula. In order to form the needle cover, the user grips the circumferential ends of the pivoting side portions with his/her fingers or a special tool and pivots them towards each other. Because for this purpose, the user has to grip the upper sides of the pivoting side portions which represent the outer side of the needle cover as the side portions are pivoted towards each other, the proximal end of the cannula is always covered by the side portions, such that the danger of an unintentional pricking injury is effectively reduced. The danger of unintentional pricking injuries is additionally reduced by the fact that the pivoting movement represents a movement which is directed generally away from the proximal end of the cannula.

By forming the cannula support in accordance with the present invention, legal conditions, working regulations and the like can also be effectively kept; such regulations increasingly prohibit the attachment of a separate cylindrical protective sleeve to the injection needle to cover it.

The form of a cannula support in accordance with the invention is advantageously simple, such that it can be manufactured cost-effectively and operated simply and reliably. In particular, the cannula support can be designed to be disposable, in which case the cannula support is removed from the injection or infusion device and disposed of after the needle cover has been formed. Providing the needle cover is formed by pivoting together the pivoting side portions, however, the cannula support can also be used repeatedly.

In one embodiment, the pivoting side portions project radially outwards from the cannula receptacle, point-symmetrically with respect to a longitudinal axis of the cannula. In this way, the pivoting movement of the side portions is symmetrically guided, such that front circumferential ends automatically come to abut each other near the longitudinal axis of the cannula support.

In order to form a needle cover, the pivoting side portions comprise connecting elements which connect the side portions to each other when the needle cover is formed, such that said connection can only be released with difficulty or, in some embodiments, not at all. The connecting elements may be arranged at the circumferential end of each of the pivoting side portions. Alternatively, the connecting elements can be arranged on the side portions at a suitable position, for example, in the form of spring-elastic latches which project from a facing side of a side portion, and in a folded-together needle protecting position grips behind an outer edge of an opposing side portion.

In some embodiments, the circumferential ends of the pivoting side portions each comprise a protrusion which projects substantially perpendicularly from the side portion such that, when the side portions are pivoted together, the protrusions form a covering area for covering the tip of the needle, wherein the covering area is orientated substantially parallel to the upper rim of the cannula support. The width of the protrusions substantially corresponds to the width of the side portions and is dimensioned such that the tip of the needle is sufficiently covered to reliably rule out an unintentional needle pricking injury.

The length of the protrusion can in each case substantially correspond to the outer radius of the cannula support. In this case, the needle cover would exhibit an overall rectangular profile in its folded-together needle protecting position.

In accordance with a preferred embodiment, the length of the protrusions is smaller than the maximum outer radius of the cannula support such that, when the side portions are pivoted together such that the distances between the side areas substantially correspond to the outer radius of the cannula support, the connecting elements do not yet co-operate to latch the needle protecting position. An advantage of this embodiment is that the cannula support comprising the needle cover can be stored in a folded-together transport position in which the maximum outer dimensions of a packaging structure substantially correspond only to the maximum outer dimensions of the cannula support.

In this preferred embodiment, the needle cover exhibits a substantially trapezoid profile in its folded-together needle protecting position, said profile being due to a kink in the side portions, substantially at the level of a base of the cannula support.

Preferably, the side portions are elastically connected to the cannula support, such that a restoring force acts which unfolds the side portions into a standard position in which the side portions project substantially radially outwards, perpendicular to the longitudinal axis of the cannula support. This is advantageous since, when the cannula support is removed from a packaging structure, the side portions do not have to be guided back by hand before the injection needle is injected into the tissue.

Other objects, advantages and features of the present invention will be identified and understood with reference to the following description, the accompanying drawings and the expanded claims.

BRIEF DESCRIPTION OF THE DRAWINGS

The invention will now be described by way of an example and by referring to the enclosed drawings, in which.

In the figures, identical reference numerals indicate identical or identically-functioning elements and functional groups.

DETAILED DESCRIPTION

Figure 1:
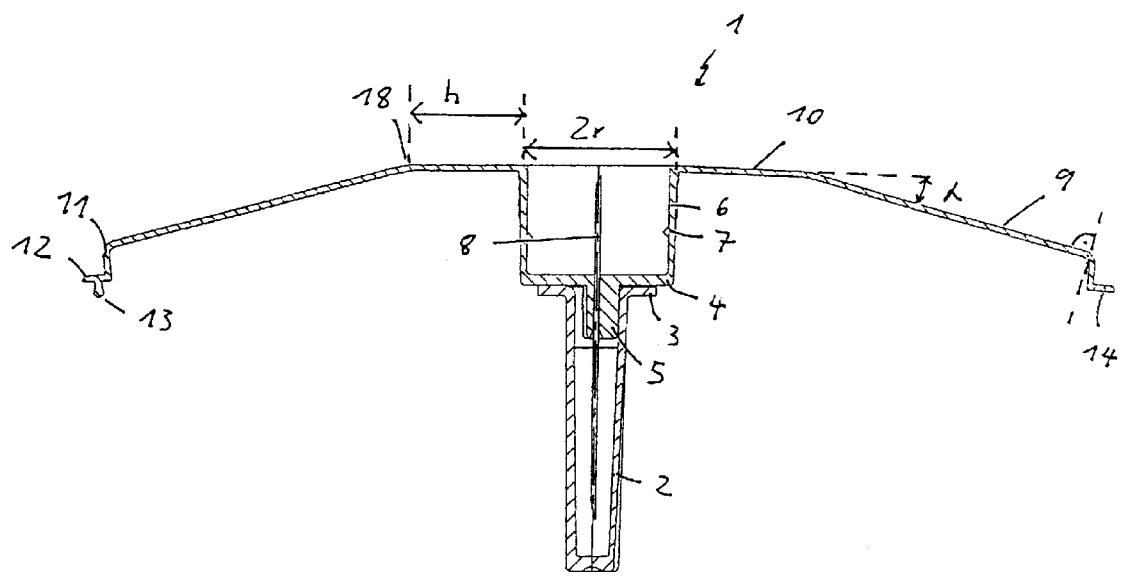
FIG. 1 is a cross-sectional view of a cannula support in accordance with the invention, in an unfolded resting position.

FIG. 1 shows a cross-sectional view of a cannula support in accordance with the invention, in an unfolded resting position. The cannula support, indicated as a whole by 1, defines an internal or inner volume, also referred to as a receptacle, formed by side walls 6 and a base 4 of the cannula support.

On the central region of the base 4, a protrusion extends in the longitudinal direction and comprises a through-bore, into which the injection needle 8 is inserted fluid-tight. The injection needle 8 and connecting technologies for connecting the injection needle 8 to the cannula support 1 are sufficiently well known from the prior art. In accordance with a preferred embodiment, the injection needle 8 is a 31-gauge injection needle.

The injection needle 8 protrudes via its distal end into the inner volume of the receptacle. Locking or connecting elements 7 for connecting to an injection or infusion device are situated on the inner side of the receptacle. The cannula support can, for example, be attached to a disposable pen. Conventional circumferential protrusions, ribs, hooking elements or the like, such as are sufficiently well known from the prior art, may be used as locking elements 7. The cannula support 1 shown is either attached directly to the injection or infusion device, in which case the distal end of the injection needle 8 preferably pierces a septum or a membrane of a container for the product to be injected, for example an ampoule, or is attached to an adapter which is then attached to an injection or infusion device in a known way.

The proximal end of the injection needle 8 protrudes beyond the base 4 of the cannula support 1 and essentially pre-sets the depth of penetration of the injection needle 8. When injecting the injection needle into the tissue, the protrusion 5 can serve as a support area onto the tissue.

Prior to use, a protective cap 2 is placed on the cannula support 1, the cap tightly surrounding either the protrusion 5 or the side walls 6 with its side walls, in order to reliably cover the proximal end of the injection needle 8 and reliably rule out potential injury.

In the resting position of the cannula support 1 shown in FIG. 1, at least two pivoting side portions 9 protrude from the side walls 6, preferably in a radial direction. The pivoting side portions 9 run substantially in a straight line and each comprise locking or connecting elements 13, 14 at their front circumferential end, which can co-operate and connect the pivoting side portions 9 to each other in the folded-together arrangement shown in FIG. 2. The connecting elements 13, 14 preferably form a connection between the pivoting side portions 9 which can only be released with difficulty, such that the proximal end of the injection needle 8 is no longer freely accessible. Suitable locking elements, latching elements, hooking elements, and also screwing elements can be used as connecting elements; any suitable connecting elements may be used, including those known in the prior art. The connecting elements 13, 14 are preferably adjusted to each other such that the connection between the pivoting side portions 9, which in some embodiments, can only be released with difficulty or preferably not at all, is formed simply and reliably by guiding the lateral abutting areas 12 together and meshing the connecting elements 13, 14. In the embodiment shown in the figures, the connecting element 13 is formed by a tear-shaped attachment which meshes with a circular opening 14 on the corresponding abutting area 12, wherein the attachment 13 elastically expands the opening 14 when inserted into it, and the opening 14 surrounds the taper of the attachment 13 such that the knob 13 can no longer be removed, from the opening 14.

Figure 3:
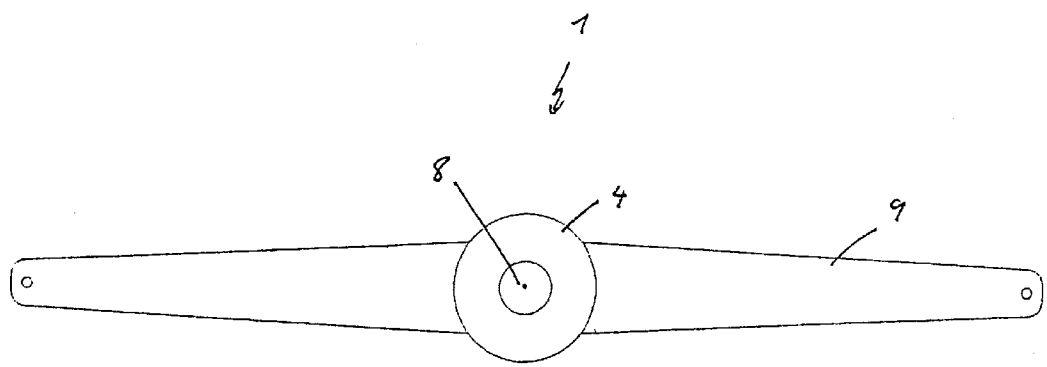
FIG. 3 is a rear top view of the cannula support in accordance with the invention, in accordance with FIG. 1.

As can be gathered from the top view in FIG. 3, the two pivoting side portions 9 extend point-symmetrically to the injection needle 8 and in a substantially radial direction. Instead of the two pivoting side portions 9 shown, more pivoting side portions 9 can also be provided. Preferably, these should also be arranged point-symmetrically to the injection needle 8, such that after use, i.e., after injection or infusion, the pivoting side portions 9 can simply be gripped and pivoted evenly and symmetrically towards each other. In the embodiment shown in FIG. 3, comprising two pivoting side portions 9, these can, for example, be gripped between the thumb and forefinger and moved towards each other by pinching the two fingers together. The point-symmetrical arrangement of the pivoting side portions enables them to be guided together evenly and symmetrically, such that the two abutting areas 12 on the longitudinal axis of the injection needle 8 come to abut each other and cover the end of the needle. Instead of with the fingers, the pivoting side portions 9 can of course also be gripped and guided together using a suitable tool.

As shown in the cross-sectional view in FIG. 1, the pivoting side portions 9 initially run, starting from the side walls 6, substantially perpendicular to the side walls 6. After a length "h," which substantially corresponds to the level of the side walls 6 of the cannula support 1, the pivoting side portions 9 are kinked, preferably at an angle α such as shall be described below.

Figure 2:
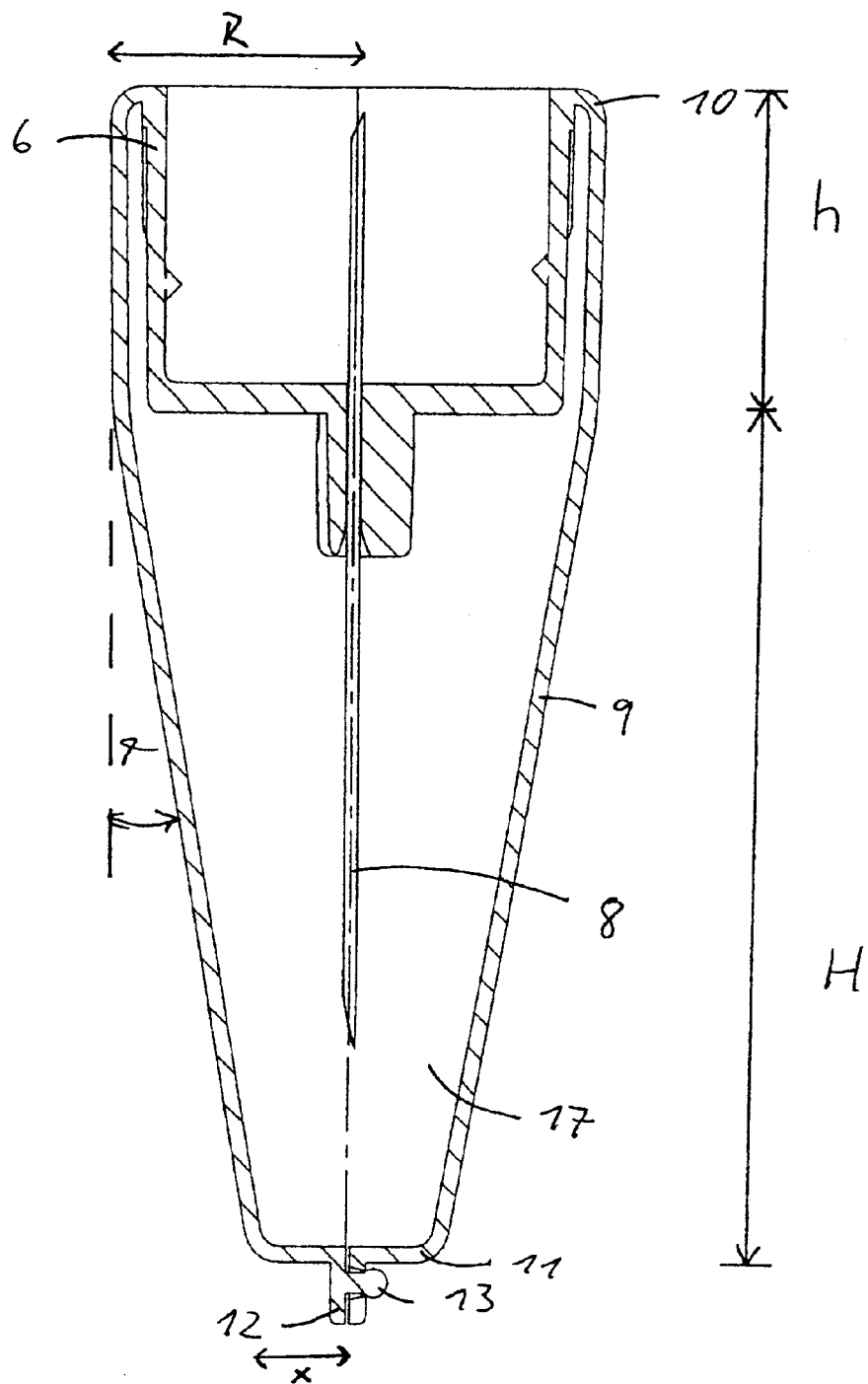
FIG. 2 is a cross-sectional view of a cannula support in accordance with the invention, in a folded-together needle covering position, for covering a proximal end of an injection needle.
Figure 4:
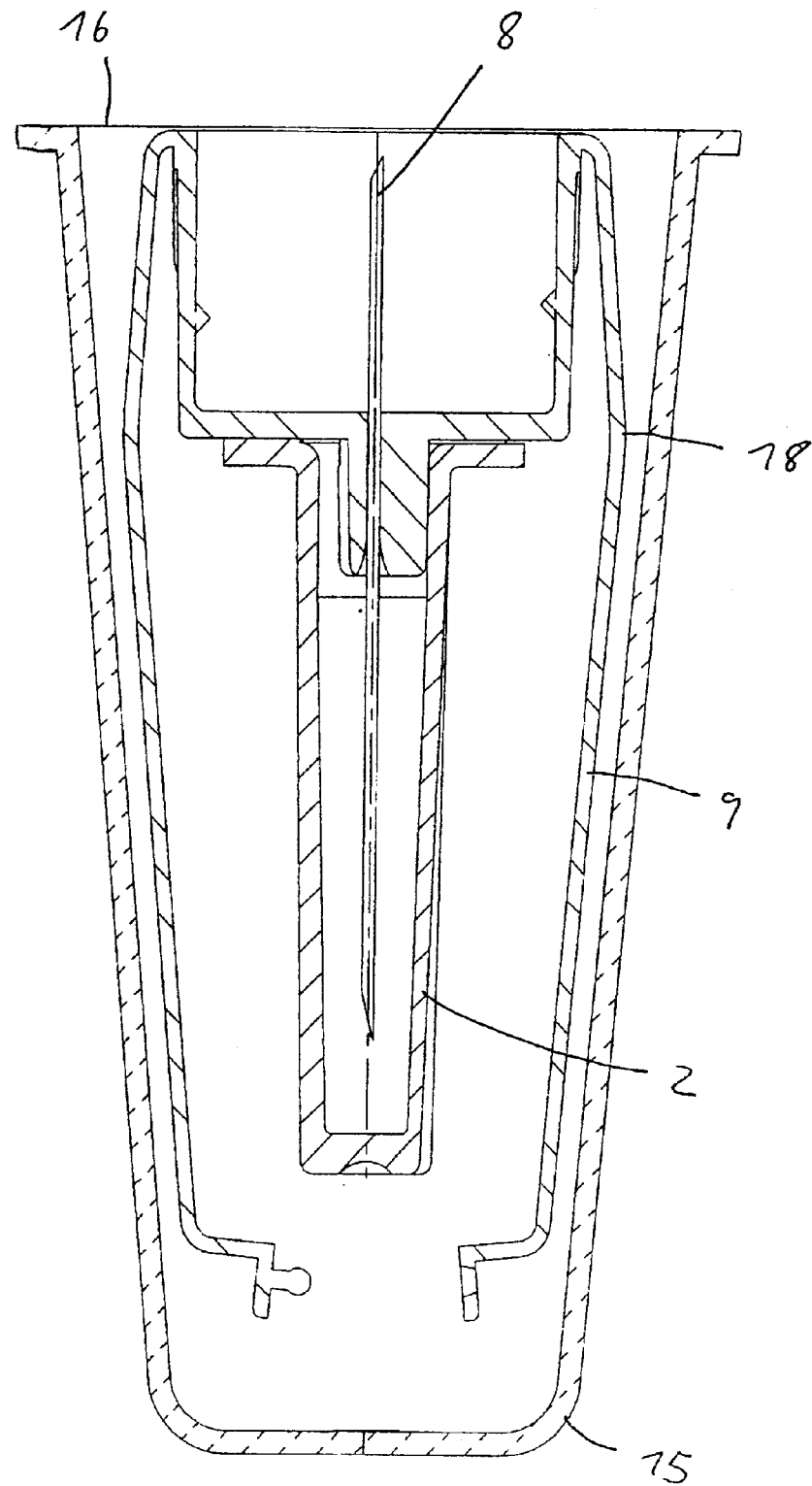
FIG. 4 is a cross-sectional view of a packaging structure in accordance with the invention, in which a cannula support is inserted into the packaging in a folded-together transport position, and the packaging is then sealed.

In the region 10 running substantially perpendicular to the side walls 6, one or more weak regions are provided near the side wall 6, such that the pivoting side portions 9 can substantially be pivoted 90° towards each other, substantially by bending them round, as shown in FIGS. 2 and 4. Measures for bending material in this way are sufficiently well known from the prior art. One or more circumferential grooves (not shown) can for example be provided in the region 10 near the side walls 6. The region 10 can also be formed as a so-called living or film hinge or hinges.

After the kink 18, the pivoting side portions 9 extend substantially in a straight line up to their circumferential ends. As shown in FIG. 1, the pivoting side portions 9 are kinked twice at the circumferential end by substantially 90°, such that a protrusion 11 and an abutting area 12 are formed, each provided with a connecting element 13 or 14. As can be gathered from FIG. 1, the protrusion 11 encloses an angle to a perpendicular line onto the pivoting side portion 9 in the region of the kink, said angle preferably corresponding to the angle α still to be described below. The abutting area 12 extends substantially perpendicular to the protrusion 11. The knob 13 extends substantially perpendicular to the abutting area 12.

FIG. 2 shows the cannula support 1 in a folded-together needle covering position in which the pivoting side portions 9 are connected by means of the connecting elements 13, 14 such that they can only be released with difficulty, and so as to cover the proximal end of the injection needle 8. As can be gathered from the top view in FIG. 3, the pivoting side portions 9 exhibit a sufficient circumferential width that, in the arrangement in FIG. 2, the proximal end of the injection needle 8 is no longer accessible from outside the needle cover. In this way, injuries can be effectively avoided. The connecting elements 13, 14 preferably only co-operate with each other at a comparatively small distance between the abutting areas 12, such that the needle covering position is only actually latched towards the end of the pivoting movement. In this way, accidentally latching the needle covering position is avoided.

As shown in FIG. 2, the pivoting side portions 9 form, in the folded-together needle covering position, a substantially trapezoid space 17 formed by the base 4 of the cannula support 1, the substantially flush protrusions 11 and the side walls subsequent to the kink 18. As can be gathered from FIG. 2, the protrusions 11 run substantially parallel to the upper rim of the cannula support 1 in the folded-together arrangement, while the two abutting areas abut one another face-on and extend substantially parallel to the longitudinal axis of the injection needle 8.

The side walls of the pivoting side portions subsequent to the kink 18 enclose an angle to the regions 10 extending substantially parallel to the side walls 6 of the cannula support 1, said angle likewise corresponding to the angle α still to be described below.

The angle α described above is calculated as follows: if R corresponds to the largest outer radius of the cannula support 1 in the folded-together needle covering position shown in FIG. 2, i.e., the distance between the section of the pivoting side portions 9 extending parallel to the side wall 6 and the longitudinal axis of the injection needle, and if the protrusion 11 of length x are arranged at a distance H to the base 4 of the cannula support 1 (FIG. 2), then the angle α is given by the following formula:

$$\alpha \approx \arctan((R-x)/H)$$

Expediently, the angle 2 is in the range 2° to 18°, preferably in the range 5° to 15°, and even more preferably in the range 8° to 12°.

On the basis of the chosen angle α, the abutting areas 12 in the folded-together protective arrangement shown in FIG. 2 automatically come to abut parallel and therefore face-on, such that the connecting elements 13, 14 can be connected to each other substantially perpendicular to the common effective connection. In addition, the protrusions 11 substantially form a plane running parallel to the upper rim of the cannula support 1.

The proximal end of the injection needle 8 is thus protected by the circumferential ends of the pivoting side portions 9 and their form. For even more effective protection, the number of pivoting side portions 9 can be increased further, for example to three or four side portions. A point-symmetrical arrangement of the side portions 9 with respect to the injection needle is preferably retained in this embodiment.

The pivoting side portions 9 can, of course, also run in a straight line without the kink, in which case the length of the protrusions 11 would correspond to the radius R and the needle cover would exhibit an overall rectangular profile in its needle covering position.

FIG. 4 shows the cannula support 1 in a folded-together transport position, in which the cannula support 1 can be inserted into a truncated, tapered packaging body 15, and in which the connecting elements 13, 14 are not yet meshing. In order to reach this position, the pivoting side portions 9 are moved towards each other until the maximum outer diameter of the folded-together cannula support corresponds to the inner diameter of the truncated, tapered packaging body 15. The cannula support 1, in its transport position, can then be inserted into the packaging body 15. In order to ensure the sterility of the resultant packaging structure, the upper end of the packaging body 15 is sealed, for example by means of a sealing film 16, a metal film, a blistering or the like.

As shown in FIG. 4, the pivoting side portions 9 subsequent to the kink 18 substantially abut the side areas of the truncated, tapered packaging body 15. The abutting areas 12 enclose an angle with a line parallel to the longitudinal axis of the injection needle, the angle substantially corresponding to the angle α described above.

In the transport position shown in FIG. 4, the injection needle 8 is covered by a protective cap 2. The latter is formed to be substantially cylindrical and via its distal end tightly surrounds the protrusion 5 or the side walls 6 of the cannula support 1, such that injury can be effectively prevented at the proximal end of the injection needle 8.

Figure 5:
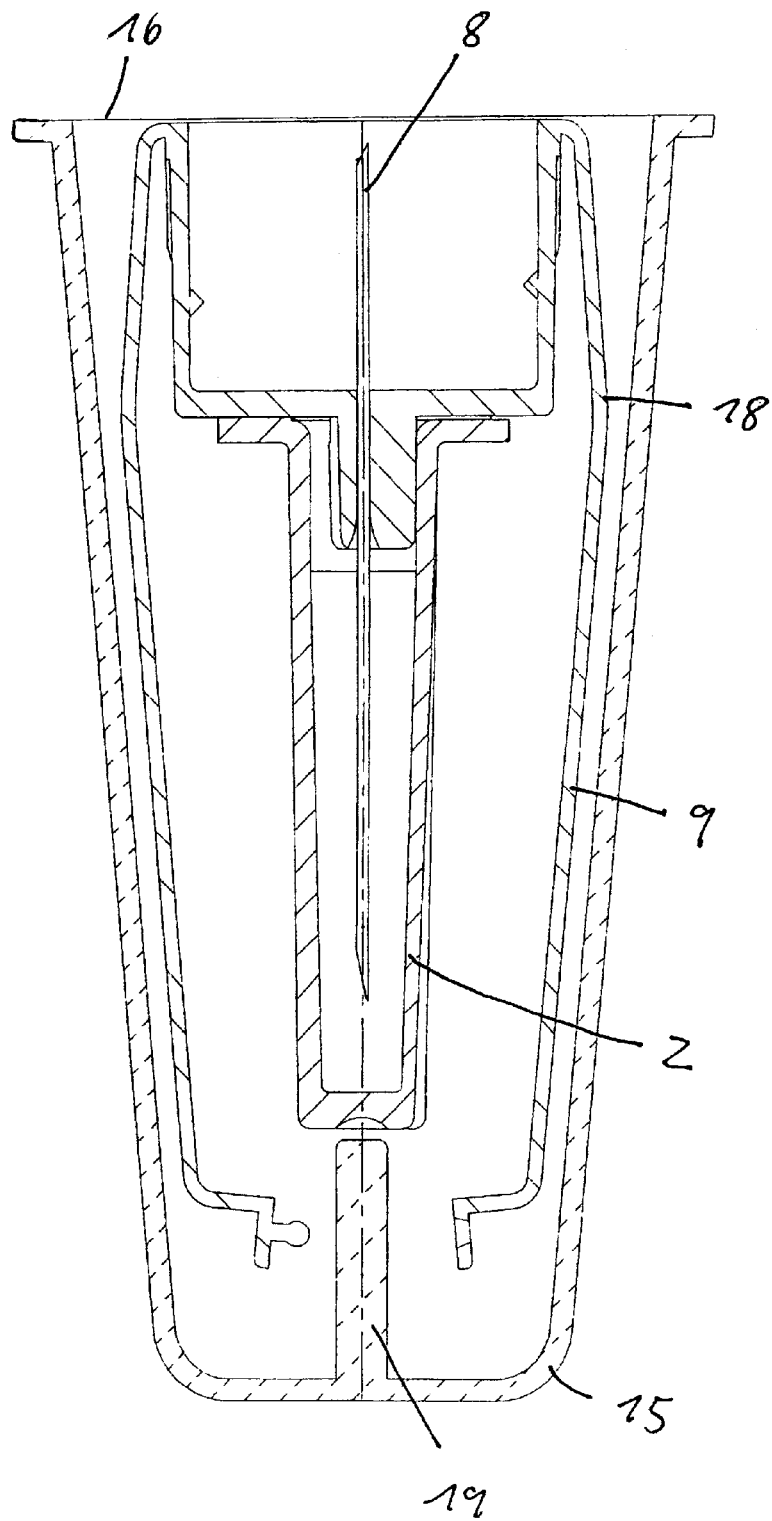
FIG. 5 shows a cross-sectional view of another embodiment of a packaging structure in accordance with the invention.

In the transport position in FIG. 4, the pivoting side portions 9 are supported, due to their elasticity, on the side areas of the truncated, tapered packaging structure 15. In order to even more reliably prevent the connecting elements 13, 14 from unintentionally meshing (in which case a needle cover which can only be released with difficulty would then unintentionally already be formed), an accommodating element 19 can be provided on the base of the packaging body 15 in accordance with the further embodiment shown in FIG. 5, said element 19 accommodating or splaying apart the abutting areas 12 and/or the protrusions 11. To this end, stays, ribs or the like can be provided as the accommodating element.

The use of a cannula support in accordance with the present invention will now be described.

Firstly, the protective cap 2 is attached via the proximal end of the injection needle 8, in the relaxed resting position shown in FIG. 1. The pivoting side portions 9 are then gripped and guided together up to the transport position shown in FIG. 4. The cannula support 1 is then vertically inserted into the packaging body 15 until the protrusions 11 and/or the abutting areas 12 abut the base or the accommodating element 19 of the packaging body. The packaging body is then sealed by means of a protective film, a metal film, a blistering 16 or the like, to form a packaging structure. The cannula support I or packaging structure is stored in the transport position shown in FIG. 4, sterile until its intended use.

In order to use the cannula support 1, the seal 16 is removed by pulling it off and an injection or infusion device is then attached to the cannula support 1 from above and connected firmly to it, for which the locking or connecting elements 7 serve. When attaching the injection or infusion device, the distal end of the injection needle 8 can pierce a septum or membrane of a container for the product to be injected. The product to be injected, for example, a medicine or a diagnostic liquid, is stored in the container, preferably an ampoule. A preferred application of the cannula support in accordance with the invention is administering insulin or hormone by means of an injection pen. The cannula support 1 can also be firstly attached to an adapter (not shown) instead of directly to the injection or infusion device, said adapter then being connected to the device in a known way.

In order to facilitate attaching the cannula support 1, the truncated, tapered packaging structure can be accommodated in a suitable holder, such that the cannula support 1 can be attached with sufficient force.

In order to be used, the injection or infusion device together with the attached cannula support 1 is removed vertically upwards out of the packaging body 15. As it is removed, the pivoting side portions 9 slide along the obliquely running side walls of the truncated, tapered packaging body 15, thus expanding increasingly until they unfold into the resting position shown in FIG. 1. The protective cap 2 is removed before the injection needle 8 is injected into the tissue.

Once the injection needle 8 is removed from the tissue, the cannula support 1 again assumes the resting position shown in FIG. 1, in which the pivoting side portions 9 extend substantially radially outwards.

The circumferential ends of the pivoting side portions 9 are then gripped by hand or by means of a suitable tool and then moved towards each other until the abutting areas 12 come to abut each other and the connecting elements 13, 14 connect the pivoting side portions 9 to each other, in some embodiments, in a way which cannot be released.

In this way, the proximal end of the injection needle 8 can be simply covered in accordance with the invention, without a protective cap having to be placed on the injection needle 8 again. In this way, pricking injuries can be effectively ruled out and legal conditions or regulations can easily be kept, for example, the ban on re-attaching a protective cap to the injection needle 8.

The cannula support 1 is made from a conventional plastic, which at least in the region 10 is sufficiently flexible to enable the pivoting side portions 9 to be guided together without the material breaking. Suitable materials are, for example: polypropylene; polyethylene; polyoxymethylene (POX). Any injection needle diameter required in each case can of course be used for the injection needle 8, for example, the injection needle 8 can be a 31-gauge injection needle. The cannula support can of course also represent any other cannula suitable for injecting or infusing, instead of the injection needle described above.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A cannula support for connection to an injection or infusion device, the cannula support comprising a cannula, a receptacle for the cannula and at least two pivoting side portions which project radially outwards from said receptacle, point-symmetrically with respect to a longitudinal axis of the cannula, and which may be pivoted towards each other, forming a needle cover with an enclosed proximal end for covering a proximal end of the cannula, wherein each pivoting side portion has a connecting element near its proximal end, the connecting element comprising an abutting area with an integral attachment feature, wherein at least one of the integral attachment features extends substantially perpendicularly from its abutting area and the abutting areas abut against each other when the side portions are pivoted together to form the needle cover and the integral attachment features are engaged with each other.

2. The cannula support as set forth in claim 1, wherein said pivoting side portions comprise weak regions running substantially in a circumferential direction, in a connecting region with the receptacle, such that the pivoting side portions are substantially parallel to portions of the receptacle when the needle cover is formed.

3. The cannula support as set forth in claim 1, wherein the pivoting side portions have a circumferential end and the connecting elements cooperate when the needle cover is formed, such that the pivoting side portions are connected such that they can only be released with difficulty or not at all.

4. The cannula support as set forth in the claim 3, wherein the connecting elements are locking elements.

5. The cannula support as set forth claim 3 further comprising a protrusion at the proximal end of each pivoting side portion, the protrusion running between the proximal end and its abutting area, wherein at a distance h from the receptacle which corresponds to the level of the receptacle, the pivoting side portions are each kinked at an angle α, wherein:

$$\alpha \approx \arctan((R-x)/H)$$

and wherein:

R corresponds to the largest outer radius of the cover in a folded-together protective (arrangement (FIG. 2);

x corresponds to the length of the protrusions; and

H corresponds to the distance between the protrusions and a proximal end of the receptacle in a folded-together needle protecting position of the side portions.

6. The cannula support as set in forth claim 5, wherein the protrusions each enclose the angle α to a perpendicular line onto the respective pivoting side portion in the region of the protrusion.

7. The cannula support as set forth in claim 1, wherein the needle cover exhibits a substantially trapezoid profile when in the needle covering position.

8. The cannula support as set forth in claim 3, further comprising a protrusion at the proximal end of each pivoting side portion, the protrusion running between the proximal end and its abutting area, the abutting areas extending substantially parallel to a longitudinal axis of the cannula and the protrusions extending substantially parallel to an upper rim of the cannula support.

9. The cannula support as set forth in claim 1, further comprising a protective cap removably placed on the receptacle to cover the proximal end of the cannula.

10. The cannula support as set forth in claim 1, wherein the cannula is a 31-gauge needle.

11. A packaged cannula support comprising:

a cannula support comprising a cannula and at least two relatively pivoting side portions; and a packing structure comprising a truncated, tapered packaging body adapted to accommodate at least a portion of the cannula support, wherein the two pivoting side portions are in a folded-together transport position and are located in the tapered packaging body.

12. The packaged cannula support as set forth in claim 11, further comprising an accommodating element for holding the pivoting side portions in a region of the packaging body to prevent the connecting elements from meshing when the cannula support is accommodated by the packaging structure.

13. The packaged cannula support of claim 12, wherein the pivoting side portions abut the packaging body when the cannula support is inserted into the packaging body.

14. The packaged cannula support of claim 11, wherein the packaging body further comprises a seal for sealing the cannula support within the packaging body and seal.

15. A packaging structure for a cannula support comprising a receptacle having two relatively pivoting side portions each having an end including a connecting element, said packaging structure comprising a tapered truncated packaging body having side walls, a seal for sealing the body, and an accommodating element, wherein when the cannula support is in the packaging structure, the pivoting side portions abut the side walls such that the pivoting side portions are pivoted toward each other and the accommodating element prevents the connecting elements from being connected.

16. A cannula support for connection to an injection or infusion device, the cannula support comprising a cannula, a receptacle for the cannula and at least two pivoting side portions which project from said receptacle and which may be pivoted towards each other, forming a needle cover covering a proximal end of the cannula, wherein said pivoting side portions have a circumferential end and each includes connecting elements co-operating when the needle cover is formed, such that the pivoting side portions are connected such that they can only be released with difficulty or not at all, wherein said circumferential ends of the pivoting side portions each (include a protrusion and an abutting area which extends substantially perpendicular to said protrusion and is respectively provided with a connecting element, wherein at a distance from the receptacle which corresponds to the level of the receptacle, the pivoting side portions are each kinked at an angle α, wherein:

$$\alpha \approx \arctan((R-x)/H)$$

and wherein:

R corresponds to the largest outer radius of the cover in a folded-together protective arrangement (FIG. 2);

x corresponds to the length of the protrusions; and

H corresponds to the distance between the protrusions and a proximal end of the receptacle in a folded-together needle protecting position of the side portions.

17. The cannula support as set forth in claim 15, wherein the protrusions each enclose the angle α to a perpendicular line onto the respective pivoting side portion in the region of the protrusion.

* * * * *

UNITED STATES PATENT AND TRADEMARK OFFICE
CERTIFICATE OF CORRECTION

PATENT NO. : 6,736,800 B2
DATED : May 18, 2004
INVENTOR(S) : Christoph Rindlisbacher It is certified that error appears in the above-identified patent and that said Letters Patent is hereby corrected as shown below:

Column 10,
Line 28, please delete "(include" and insert -- include --.
Line 43, please delete "claim 15" and insert -- claim 16 --.

Signed and Sealed this

Seventh Day of September, 2004

JON W. DUDAS
*Director of the United States Patent and Trademark Office*